(12) United States Patent
Geipel et al.

(10) Patent No.: US 9,248,230 B2
(45) Date of Patent: Feb. 2, 2016

(54) SENSOR DEVICE FOR USE IN A MEDICAL FLUID DELIVERY SYSTEM

(71) Applicant: Roche Diagnostic International AG, Rotkreuz (CH)

(72) Inventors: Andreas Geipel, Heddesheim (DE); Pascal Grossenbacher, Bern (CH); Philipp Michel, Kirchlindach (CH); Ulrich Haueter, Grosshoechstetten (CH)

(73) Assignee: Roche Diagnostics International AG, Rotkreuz (CH)

( * ) Notice: Subject to any disclaimer, the term of this patent is extended or adjusted under 35 U.S.C. 154(b) by 313 days.

(21) Appl. No.: 14/026,808

(22) Filed: Sep. 13, 2013

(65) Prior Publication Data

US 2014/0007694 A1 Jan. 9, 2014

Related U.S. Application Data

(63) Continuation of application No. PCT/EP2012/055072, filed on Mar. 22, 2012.

(30) Foreign Application Priority Data

Mar. 22, 2011 (EP) .................................. 11159202

(51) Int. Cl.
*G01L 11/02* (2006.01)
*A61M 5/142* (2006.01)
*A61M 5/168* (2006.01)
*G01L 9/00* (2006.01)

(52) U.S. Cl.
CPC ........... *A61M 5/142* (2013.01); *A61M 5/16854* (2013.01); *G01L 9/0077* (2013.01); *G01L 11/02* (2013.01); *A61M 2205/3306* (2013.01)

(58) Field of Classification Search
None
See application file for complete search history.

(56) References Cited

U.S. PATENT DOCUMENTS

| | | | | |
|---|---|---|---|---|
| 4,759,264 | A * | 7/1988 | Danby | A61M 5/14224 92/103 SD |
| 5,712,044 | A * | 1/1998 | Fanselow | A61L 31/048 428/510 |
| 7,955,302 | B2 | 6/2011 | Haueter et al. | |
| 2005/0159708 | A1* | 7/2005 | Sidler | A61M 5/1452 604/132 |

(Continued)

FOREIGN PATENT DOCUMENTS

| | | |
|---|---|---|
| EP | 1970677 A1 | 9/2008 |
| EP | 2399626 A1 | 12/2011 |

(Continued)

OTHER PUBLICATIONS

Kohl, M.J., et al., "A Microfluidic Experimental Platform With Internal Pressure Measurements", Sensors and Actuators, A 118, (2005), pp. 212-221.

*Primary Examiner* — Andre Allen
(74) *Attorney, Agent, or Firm* — Roche Diagnostics International AG

(57) ABSTRACT

A sensor device for use in a medical fluid delivery system, or an infusion pump device, comprises a fluidic chamber with a deformable cover closing at least an area of the chamber and an optical detection system comprising at least one light emitter for emitting one or more incident light beams and a sensor unit for monitoring one or more reflected light beams is presented. In a pressurized state of the fluidic chamber, the deformable cover is deformed such that it forms an inflexion point area within the deformed cover. The one or more incident light beams emitted by the light emitter are directed on the cover such that the one or more incident light beams are reflected essentially in the inflexion point area.

18 Claims, 6 Drawing Sheets

(56) References Cited

U.S. PATENT DOCUMENTS

2009/0118667 A1  5/2009  Haueter et al.
2013/0107267 A1* 5/2013  Leuenberger ..... A61M 5/16854
                                                356/445

FOREIGN PATENT DOCUMENTS

FR      2540987 A1    8/1984
WO      2008/144693 A1  11/2008

* cited by examiner

SENSOR DEVICE FOR USE IN A MEDICAL FLUID DELIVERY SYSTEM

CROSS-REFERENCE TO RELATED APPLICATIONS

This application is a continuation of PCT/EP2012/055072, filed Mar. 22, 2012, which is based on and claims priority to EP 11159202.8, filed Mar. 22, 2011, which is hereby incorporated by reference.

BACKGROUND

The present disclosure generally relates to a sensor device for use in a medical fluid delivery system and, in particular, to an infusion pumps device, like an insulin infusion pump device, to monitor a fluidic pressure and/or detecting occlusions in a fluidic system of such system and device.

Medical fluid delivery systems for the administration of, for example, liquid medical fluids, such as infusion pump devices, are often used with patients who have a continuous, and in the course of the day varying, need of a medicine that can be administered, for example, by subcutaneous infusion. Specific applications are, for example, certain pain therapies and the treatment of diabetes. In such cases, computer controlled automated infusion pump devices are used, which can be carried by the patient on the body, and which contain a certain amount of liquid medicine in a medicine reservoir. The liquid medicine is supplied to the patient's body from the medicine reservoir through a fluidic system to an infusion cannula or an injection needle. Mostly such medical fluid delivery systems comprise a reusable unit including an actuation mechanism, a dosing mechanism, electronics for controlling the mechanisms, and the like and a disposable unit including, for example, a fluid reservoir, which is discarded after emptying the reservoir.

The liquid medicine can be obtained by a downstream pump from a flexible container. Flexible containers have the advantage of a smaller volume surplus of the container in relation to its content reducing the manufacturing costs and enabling design of infusion pump devices of smaller overall dimensions. Thus, the device cannot be seen through clothing and can be carried as comfortably as possible.

In the context of liquid medicine administration via an infusion pump device, sensor devices are used for controlling the dosing, monitoring the correct operation of the system, and for fast detection of faults and hazards, such as occluded infusion lines or cannulae, empty containers, or malfunctioning pump systems. A pressure sensor device may be in a fluid path downstream of a pump device and upstream of an infusion cannula.

Such pressure sensor devices typically comprise a microfluidic chamber filled with liquid and fluidly connected to the fluidic system. The chamber is covered by a flexible, resilient membrane such that a pressure difference between the fluidic pressure inside the sensor chamber and the outside (such as atmospheric) pressure will temporarily deform the membrane. The resulting deflection of the membrane can then be measured in order to determine the internal pressure of the fluidic system.

A suitable approach to measure the deformation of the membrane is optical detection of a light beam reflected on the membrane. The pressure sensor device includes a microfluidic chamber connected to a fluidic system comprising a rigid bottom substrate and a flexible, resilient top cover, for example, a membrane. An optical detection system measures a deformation of the cover membrane by determining the interaction of a light beam with the cover membrane. For that purpose, a light emitting device, such as, a laser diode, directs a light beam at a certain angle onto the surface of the cover membrane where it is reflected. The pressure difference between the inner volume of the micro-fluidic chamber and the outer environment acts on the cover membrane and deforms it to a certain extent depending on the pressure difference. As a result, the angle of the reflected light beam changes and the beam is transversely shifted. By monitoring the position of the reflected light beam, the deformation of the cover membrane can be measured and based on the obtained results a pressure difference value can be determined.

In one example, an insulin pump comprises a reusable unit with drive, dosing and controlling systems and a disposable unit with a flow path and a catheter tube. The flow path can be connected to the driving and dosing mechanism such that a liquid system runs from a liquid reservoir to the catheter tube. A resilient membrane is in the flow path and covers a fluidic chamber. The membrane is impinged directly by the liquid in the flow path such that it is deflected towards the reusable unit in case of a pressure increase, for example, due to an occlusion of the liquid system. The reusable unit comprises a light emitter in form of a laser diode and a photosensitive x-y sensor connected to the controlling system. The light beam of the laser diode can be directed on a rigid reflector arranged on the membrane. Alternatively, the light beam can be directed directly on the membrane surface. In this case, a small area on the surface of the membrane is metal-coated to provide good reflecting properties of the membrane. The incident light beam is focused on an area of the membrane at a distance to the center of the membrane. That means in a deflected state of the membrane the reflecting area is inclined and rounded with respect to the non-deflected state. Therefore, a reflected light beam changes direction and shape, which can be detected by the x-y sensor and is an indication for a pressure change within the liquid system.

Another infusion pump system comprises an occlusion sensor that can be used to detect when an occlusion exists in the fluid path between a medicine reservoir and the infusion site. The occlusion sensor includes a flexible membrane which can be deflected by rising pressure in the fluid path such that it touches a wall of an air cavity. The incident measurement light beam is guided through a light transmissive member to the air cavity. In a non-deflected state, the incident beam is totally reflected at the air cavity. In a deflected state, when the membrane touches the air cavity, reduced reflection occurs. The reduction of the intensity of the reflected light beam is a measurement for the pressure in the fluid path.

Since some of the parts of the pressure sensor device are in the disposable unit and other parts are in the reusable unit, the orientation of disposable and reusable part towards each other can be a critical parameter of reliable measuring results. In the known systems, the tolerances between these units must be as small as possible. For monitoring the reflected light beam in a pressure sensor according to the prior art, a detector in the optical detection system often is designed to be movable, or a multiplicity of detectors at different positions and at different angles are included in the device. Both of these aspects make such sensor devices expensive and difficult to make. A wide range of directions of reflected light beams due to the large variety or diffuse reflection angles on a membrane also requires a complex sensor array in the pressure sensor device.

Therefore, there is a need to provide an improved sensor device for use in a medical fluid delivery system, such as an infusion pump device for liquid medicines, like insulin, for monitoring pressure variations in a medical fluid delivery system, which is easy to install and indicates pressure changes or fluid path occlusion in a simple manner and overcome the drawbacks of prior art devices.

SUMMARY

According to the present disclosure, a sensor device for use in a medical fluid delivery system is disclosed. The sensor device can comprise a fluidic chamber with a deformable cover closing at least an area of the fluidic chamber, wherein, in a pressurized state of the fluidic chamber, the deformable cover can be deformed such that it can form an inflexion point area within the deformed cover and an optical detection system comprising at least one light emitter for emitting one or more incident light beams and a sensor unit for monitoring one or more reflected light beams, wherein the one or more incident light beams emitted by the light emitter can be directed on the cover such that the one or more incident light beams can be reflected in the inflexion point area.

In accordance with one embodiment of the present disclosure, a method for monitoring a pressure change in a fluidic chamber of a medical fluid delivery system using a sensor device id disclosed. The method can comprise directing one or more incident light beams on the inflexion point area of the deformable cover; detecting one or more reflected light beams reflected from the deformable cover in a non-pressurized state and a pressurized state; and comparing detection data of the non-pressurized state and the pressurized state to extract the pressure change value.

Accordingly, it is a feature of the embodiments of the present disclosure to provide an improved sensor device for use in a medical fluid delivery system, such as an infusion pump device for liquid medicine, like insulin, for monitoring pressure variations in a medical fluid delivery system, which is easy to install and indicates pressure changes or fluid path occlusion in a simple manner and overcome the drawbacks of prior art devices. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1A:
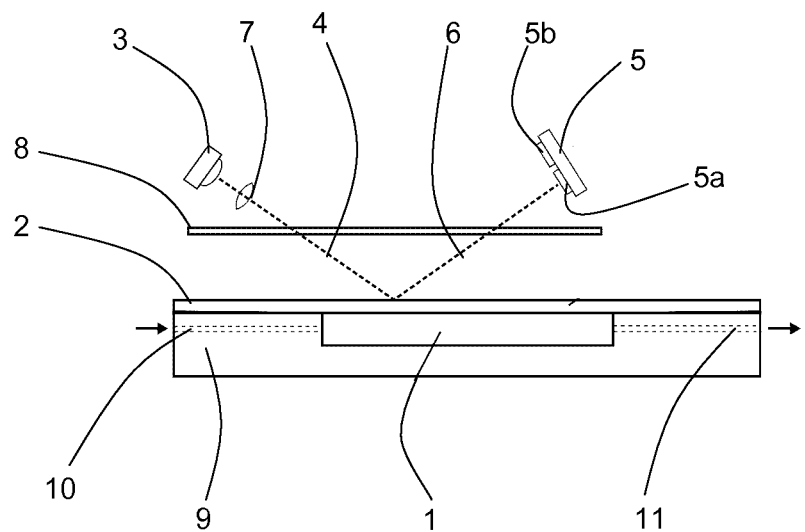
FIG. 1a illustrates a schematic cross-sectional view of a sensor device in a non-pressurized state according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A sensor device according to the present disclosure for use in a medical fluid delivery system can comprise a fluidic chamber with a deformable cover closing at least an area of the chamber and an optical detection system comprising at least one light emitter for emitting one or more incident light beams and a sensor unit for monitoring one or more reflected light beams. In a pressurized state of the fluidic chamber, the deformable cover can be deformed such that it can form an inflexion point area within the deformed cover. The one or more incident light beams emitted by the light emitter can be directed on the cover such that the one or more incident light beams can be reflected essentially in the inflexion point area.

The fluidic chamber can be part of a fluid path of an infusion pump device or a medical fluid delivery system. It can be formed, for example, as a micro-fluidic chamber in fluidic connection with such a fluid path. The cover can be placed over an opening in the fluidic chamber such that the cover can be in contact with the interior atmosphere of the chamber. Advantageously, the cover can cover an at least partially rounded opening of the fluidic chamber. The cover may be in direct contact with a fluid delivered through the fluidic chamber. But in general, it can be possible to locate a transmission volume, like a gas volume, between the fluid and the cover which can transmit pressure changes in the fluid to the cover.

In one embodiment, the fluidic chamber can be part of a disposable unit of a medical fluid delivery system and the optical detection system can be part of a reusable unit of the medical fluid delivery system. The light emitter can be for example, one or more light emitting diodes (LED) or laser diodes. Advantageously, one diode emitting one light beam of one wavelength can be enough to realize the sensor device. The sensor unit can for example be photodiodes.

The cover can be a flexible, resilient membrane cover which can be deformable or deflectable. In a normal state of operation of the sensor device or the medical fluid delivery device, i.e., a regular pressure atmosphere within the fluidic chamber, the cover in general can be essentially not deformed. In the case of a medical fluid delivery system for insulin, regular pressure can be about 200 to 2000 mbar relative pressure. This state can be a non-pressurized state of the fluidic chamber, although a specific normal pressure can always exist in the system. The non-pressurized state can be determined by a reference measurement with the optical detection system. Thus the non-pressurized state may serve as a reference state and pressure changes can be detected in respect to this reference state. In the case where the pressure within the fluidic chamber increases or decreases, the cover can be deformed due to the force of the pressure change. This state can be a pressurized state of the fluidic chamber comprising a deformed cover.

The inflexion point area can be the area where the radius of curvature of the cover can change along a line running within the cover from an edge of the cover connected to the fluidic chamber to the center of the cover. It can also be the area within the absolute value of the curvature changes sign. In this area, the curvature of the cover can be negligible and can act as an even or nearly even reflection area. In fact, when the cover is deformed and buckling to one or the other side, an inflexion line around the center of the cover can be formed.

The one or more incident light beams can be directed on the cover at an angle α. In the normal state of the cover, i.e. the non-pressurized state, the incident light beam can meet the cover in an area corresponding to a potential inflexion point, or in close vicinity of this area. While the fluidic chamber can be pressurized to a pressurized state that area can be tilted and mostly also offset translative compared to the normal state due to the deformation of the cover. Since the area can comprise the inflexion point, it can be approximately even and may act as plane reflection area for the incident light beam in the pressurized state. At the same time, it can be the area with the most angular change compared to the normal state of the cover. That can mean the one or more light beams can be reflected in the area of the cover comprising the largest change of orientation towards the incident light beams when passing from the non-pressurized state to the pressurized state. But around the inflexion point there can be a minimum sphericity negatively affecting the quality of the reflected light beam.

The sensor device can allow a maximum change in reflection of the one or more incident light beams in the pressurized state compared to the non-pressurized state of the cover and therefore can ensure accurate observation of pressure abnormalities within the fluidic chamber. The detection at the maximum deflection of the reflected light beams can enable a simple and cost-efficient construction of the sensor unit and can provide large flexibility in the arrangement of the elements of the sensor device relative to each other.

Good results can be achieved by using an incident light beam, which can essentially be a parallel light beam. Therefore, a laser diode, or a light emitting diode, comprising an optical element for parallelizing emitted light beams can be used advantageously. In the case of a parallel incident light beam and the fact that the deformed cover can be generally planar in the inflexion point area, the reflected light beam can also be basically parallel and can be focused precisely towards the sensor unit.

Depending on the light emitter used, the incident light beam may practically be a bundle of light beams, which can cover not only a point on the cover but can rather spread over an area on the cover surface. The diameter of the overall incident light beam can be selected such that an edge of the beam does not extend beyond the center point of the cover on the fluidic chamber. The diameter of the incident light beam may be about ⅓ or less of the cover diameter. It can be advantageous if it is less than about ¼ and even less than about ⅕ of the cover diameter.

In a non-pressurized state of the fluidic chamber, the one or more incident light beams can be directed on the cover at an angle α. Alternatively, the incident light beams may be focused perpendicular on a non-pressurized cover. An angled direction can provide large flexibility in the construction of the single elements of the optical detection system. Furthermore, it can be advantageous to reflect the one or more incident light beams at an inflection point area on the cover located closest to the light emitter. That can minimize the optical path of the incident light beam and can maximize the optical path of the reflected light beam from the inflection point area to the sensor unit. Therefore, the distance travelled by the reflecting light beam on the sensor unit can be maximized and the resolution of the sensor unit can be optimized.

Due to the optimized deflection of the incident light beams by the inflexion point area of the fluid chamber cover, it may not be necessary to provide a sensor unit with a large array of photodiodes. In one embodiment, the sensor unit can be a dual-element sensor comprising two photo-elements. For example, two photodiodes can be directly next to each other in one line. The incident light beam can be focused on a first photodiode, when the fluidic chamber is in a non-pressurized state, and can be focused on a second photodiode, when the fluidic chamber is in a pressurized state. That can mean when a pressure change in the fluidic chamber occurs, the reflected light beam can wander from the first photodiode to the second photodiode. From a particular pressure value on the reflected light beam can be fully focused on the second photodiode. The particular pressure value can correspond to a specific application of the sensor device. For the use of the sensor device as a pressure sensor, for example, in an infusion pump device, the reflected light beam can change from first to second photodiode within a range of pressure change of about 200 mbar to about 2000 mbar. Also, the material of the cover, or the arrangement of the two photodiodes, may be relevant pressure changes and the particular pressure value respectively.

Alternatively, the two photodiodes may be separate from each other. In this case, at least one optical element may be provided in an optical path from the inflexion point area towards one or both of a first and/or a second photodiode to direct the reflected light beam to the respective photodiode. The optical element or elements can be located such that in a non-pressurized state, the reflected light beam can hit the first photodiode directly or a first optical element can direct the beam to the first photodiode. In a pressurized state, the reflected light beam can be deflected by the inflexion point area of the cover such that it can move away from the first photodiode, or the first optical element, and instead can hit a second optical element which guides the beam to the second photodiode or can meet the second photodiode directly. A mirror element can for example be used to guide the reflected light beam.

In one embodiment, the light emitter of the sensor device can be located on a side of the cover which is curved in a convex manner in an increased pressure state of the fluidic chamber. That can mean the light emitter can direct the one or more incident light beams directly on the cover instead of first passing the interior of the fluidic chamber and the fluid delivered through the chamber. Advantageously, one side of the cover can be in fluid contact and the light emitter can be located on the other side of the cover. In this arrangement, the point of incidence of the incident light beam, which can define the inflexion point area on the cover, can be subject to a superposition of two effects when the cover changes from the normal state to the pressurized state and shaping the inflexion point or line as mentioned above. First the point of incidence can be elevated translational by a distance w and second the point of incidence can be tilted by an angle ϵ. That can mean, in the deformed state of the cover, the inflexion point area can change its angular and its translational location in respect to the non-deformed state. A distance s travelled on the sensor unit by the reflected light beams, for example, from the first photodiode to the second photodiode, can therefore be determined by the superposition in case of small elevation and deflection:

$s = 2 \cdot w \cdot \cos(\alpha) + d \cdot \tan(2\epsilon)$, wherein $\alpha$ can be defined by the angle of incidence between the incident light beam and the cover and d can be the distance from the point of incidence on the cover to sensor unit. The angle $\alpha$ may lie between about 30° to about 60° and even between about 40° to about 50°. In this range, the distance s can act basically linear to a pressure within the fluidic chamber.

Of course, the degree of tilting and elevation can depend on the material used for the cover or membrane cover respectively. The cover can be realized as a polymer foil. The polymer foil may be an integral part of the disposable unit of a delivery device or the like. Material used can be, for example, PMMA, PC, PET, PA, PSU, or COC/COP. The thickness of the cover material can be, for example, between about 50 μm and about 200 μm. In another embodiment, the cover material can be between about 80 μm and about 150 μm. The cover can reflect a sufficient portion of the incident light beam from the light emitter. Therefore, the cover material can be metalized, for example, by a layer of aluminium, chrome, silver, gold or the like. Alternatively, a metal foil comprising sufficient elasticity may be used.

According to another embodiment, an infusion pump device for use in a medical fluid delivery system can comprise a sensor device as mentioned above. The sensor device may be an integral part of a dosing unit of the infusion pump device. For example, the fluidic chamber of the sensor device can be part of a dispensing fluid path connected to a delivery opening of the infusion pump device.

According to yet another embodiment, a medical fluid delivery device can comprise a sensor device or an infusion pump device as mentioned above. The delivery device may comprise a reusable unit in combination with a disposable unit. The disposable unit can comprise, for example, a fluid reservoir and usually can be discarded after use. The reusable unit can be designed so that a disposable unit can be connected to it. Also the sensor unit may be located in the reusable unit. Advantageously, the optical detection system of the sensor device can be part of the reusable unit of the delivery device and the fluidic chamber can be part of the disposable unit of the delivery device. The disposable unit may comprise an optical element for directing the incident light beam in a predetermined angle $\alpha$ on the inflexion point area of the cover. That can mean the light emitter can be arranged in any suitable manner relative to the fluidic chamber and the cover respectively, for example, such that the emitted light can be orientated parallel or perpendicular to the cover. The parallel or perpendicular light beam can be refracted by the optical element such that light beam can be directed to the cover in the desired angle $\alpha$. Furthermore, the disposable unit of the delivery device may comprise an optical element for directing the reflected light from the inflexion point area to the sensor unit.

In one embodiment of the medical fluid delivery device, the optical elements for the light path of the incident and/or reflected light beams may be part of the disposable unit of the delivery device. For example, the optical elements may be part of a cap or covering of the fluidic chamber, which can be attached to a surrounding edge of the cover of the fluidic chamber. The optical elements can be transparent for the light of the light emitter. The optical elements can be made of amorphous polymer material, for example. The fluidic chamber and the optical elements may be made of the same material. With the use of such a disposable unit, the incident light beam of the light emitter can be orientated perpendicular to the cover on the fluidic chamber. The perpendicular light beam can be deflected by the first optical element or the covering of the disposable unit such that the incident light beam can be directed in angle $\alpha$ on the inflexion point area of the cover. After reflection of the light beam, a second optical element may focus the reflected beam onto the sensor unit or one of the photodiodes of the sensor unit respectively.

The use of optical elements can facilitate a correct positioning of the disposable and reusable units relative to each other. The optical elements can compensate a mismatch of the units within a tolerance of approximately ±0.5 mm. Therefore, a medical fluid delivery system comprising a sensor device can enable accurate observation of the functioning of the delivery system.

A pressure change in a fluidic chamber of a medical fluid delivery system can be monitored using a sensor device by directing one or more incident light beams on the inflexion point area of the deformable cover. One or more light beams reflected from the deformable cover in a non-pressurized state and a pressurized state can be detected. The detection data of the non-pressurized state and the pressurized state can be compared to extract the pressure change value. Therefore, the optical detection system can be connected to an electronic controlling system of the medical fluid delivery system. A threshold pressure level can be defined and deposited in the controlling system at which the delivery system can be shut down or an alarm can be given to indicate a critical pressure value or malfunction of the system. In the case of an occlusion in a fluidic path of the medical fluid delivery system, the threshold value may be between about 200 mbar and about 2000 mbar relative to the atmosphere. However, mostly it can be between about 500 mbar and about 1200 mbar and it even can be around 1000 mbar.

In a non-pressurized state of the fluidic chamber, a reflected light beam reflected from the non-deformed cover of the fluidic chamber can be directed on a first photo-element of the dual-element sensor and in a pressurized state of the fluidic chamber a reflected light beam reflected from the deformed cover can be directed on a second photo-element of the dual-element sensor. The threshold pressure level may be reached as soon as the reflected beam fully left the first photo-element and fully hits the second photo-element. Alternatively, the threshold pressure level may be achieved as soon as a particular value of light intensity is detected on the second photo-element. In a still further alternative, the difference of the light intensity detected by the two photo-elements can be evaluated.

The sensor device can offer reliable and simple detection of pressure changes and/or occlusion in a fluid path of the system. It can allow a space saving structure of a delivery system and can reduce complexity of detection algorithms. Also the sensor device can easily and safely be used in combination with reusable and disposable units of the system and can be produced cost-efficiently.

Referring initially to FIGS. 1 to 10, the basic elements and the function of a sensor device and a method for monitoring pressure changes in an infusion pump device and a medical fluid delivery system are explained with reference to schematic illustrations showing features of the disclosure.

FIG. 1a shows a schematic cross-sectional view of a sensor device for use in a medical fluid delivery system. The sensor device can comprises a fluidic chamber 1 with a deformable cover 2 closing at least an area of the chamber. An optical detection system of the sensor device can comprise a light emitter 3, such as an LED for example, for emitting incident light beams or a bundle of light beams 4 and a sensor unit 5 for monitoring one or more reflected light beams 6. An optional optical element 7, such as, a collective lens, an aperture, or the like, can be arranged in the light path of the incident light beam 4 to parallelize the emitted light of the LED 3. The sensor unit 5, for example, a dual-element sensor, can comprise a first photodiode 5a and a second photodiode 5b arranged directly next to each other. The optical detection system can be in a reusable unit of a medical fluid delivery system wherein the incident light beam and the reflected light beam can pass through an optical window 8 of the reusable unit to the exterior of the reusable unit.

The fluidic chamber 1 can be part of a fluidic module 9 comprising a cavity, which can be covered by the deformable cover 2 on one side. The fluidic chamber 1 can be a microfluidic chamber. A fluid inlet 10 can connect the fluidic chamber 1 to a fluid reservoir (not shown) and a fluid outlet 11 can lead from the fluidic chamber 1 to a patient. The fluid inlet 10, the fluidic chamber 1 and the fluid outlet 11 can be part of a fluidic path leading from the fluid reservoir to the patient. The cover may be, for example, glued or welded to the surface of the fluidic module 9. The cover 2 can cover an at least partially rounded opening of the fluidic chamber 1. The opening can be substantially fully circular facilitating the detection of the cover in a pressurized state and establishment of a gentle curvature of the cover. The fluidic module 9 can be part of a disposable unit of the medical fluid delivery system that can be attached to the reusable unit.

In FIG. 1a, the fluidic chamber 1 can be in a non-pressurized state, which can mean the pressure value in the chamber can correspond to normal operation of the medical fluid delivery system. The deformable cover 2 cannot be deflected but can stretch planar over the fluidic chamber 1. The incident light beam 4 can be reflected on the planar surface of the deformable cover 2 such that the reflected light beam 6 can be directed on the first photodiode 5a of the sensor unit 5. The photodiode 5a can send a signal to an electronic control system (not shown) of the medical fluid delivery system to indicate a normal pressure condition within the fluidic path.

Figure 1B:
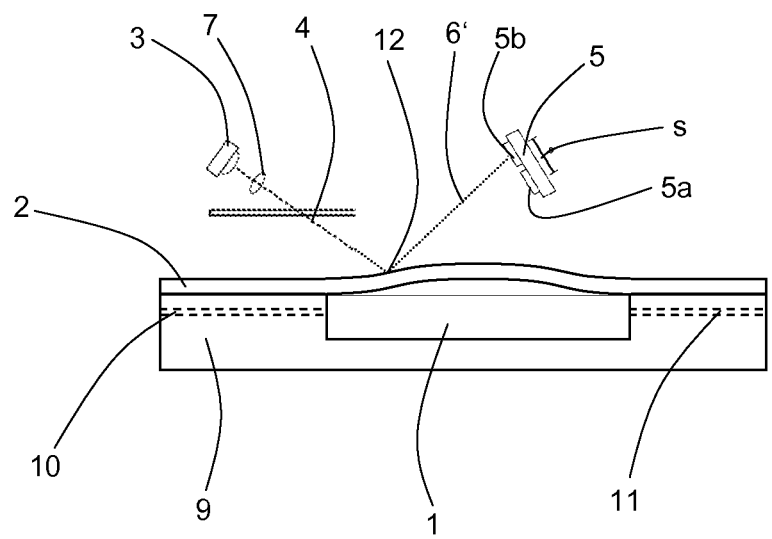
FIG. 1b illustrates a schematic cross-sectional view of the sensor device according to FIG. 1a in a pressurized state according to an embodiment of the present disclosure.

In FIG. 1b, the fluidic chamber 1 is shown in a pressurized state. As shown, the pressure within the fluidic chamber 1 increased such that the deformable cover 2 can be deformed and can form an inflexion point area 12 within the cover surface covering the fluidic chamber 1. The deformed cover 2 can have a convex shape with respect to the optical detection system and the reusable unit respectively when the pressure within the fluidic path increases. The incident light beam 4 emitted by the light emitter 3 can be directed on the cover 2 such that the incident light beam 4 can be reflected essentially in the inflexion point area 12, such as, for example, in the inflexion point. The reflected light beam 6' can be deflected due to the change in orientation of the deformable cover 2 in respect to the non-deformed cover by a distance s. The reflected light beam 6' can now be directed on the second photodiode 5b of the sensor unit 5. The photodiode 5b can send a signal to the electronic control system indicating a pressure change in the fluidic chamber 1 and, therefore, in the fluidic path.

Figure 2A:
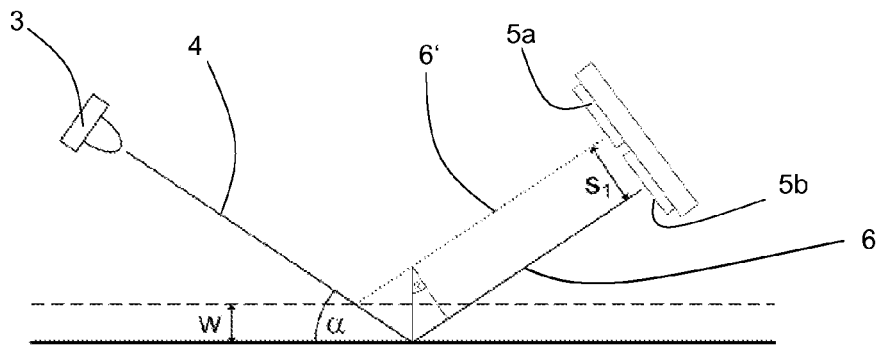
FIG. 2a illustrates schematically a translational offset of the cover in a pressurized state according to an embodiment of the present disclosure.
Figure 2B:
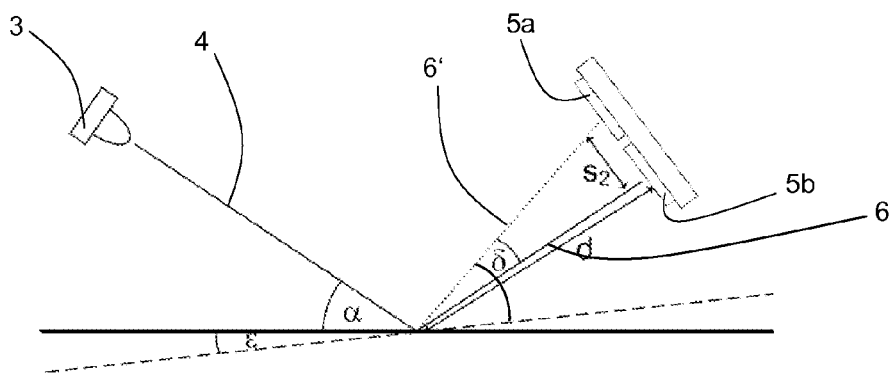
FIG. 2b illustrates schematically an inclination of the cover in a pressurized state according to an embodiment of the present disclosure.
Figure 2C:
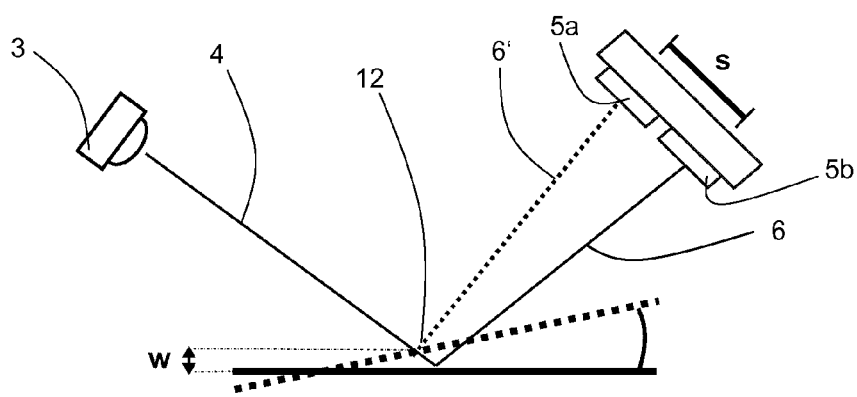
FIG. 2c illustrates schematically a superposition of the translational offset and the an inclination of the cover in a pressurized state according to an embodiment of the present disclosure.

In FIGS. 2a-c, the change in reflection of the incident light beam 4 due to the deformation of the cover 2 is explained. In comparison to the normal non-pressurized state, in the pressurized state, the deformable cover can be lifted translational by a height w, as shown in FIG. 2a. That can mean the reflected light beam can be shifted and offset by a distance $s_1$, which can be defined by $s_1 = 2 \cdot w \cdot \cos(\alpha)$, wherein α can be the incident angle between the incident light beam and the deformable cover. The reflected light beam 6' of the pressurized state can be shifted from the first photodiode 5a in the direction of the second photodiode 5b by the distance s1. Also the deformable cover 2 can be tilted by an angle ε relative to the non-pressurized state, which can change the incident angle of the incident light beam, as shown in FIG. 2b. In the inflexion point area, the curvature of the deformed cover can change. The surface of the deformed cover can be approximately even and the angle ε can be approximately constant in this area. The direction of the reflected light beam can be changed by an angle δ, which can be defined by $\delta = 2 \cdot \varepsilon$. That can lead to a shift $s_2$ on the sensor unit 5 from the first photodiode 5a in the direction of the second photodiode 5b, wherein $s_2 = d \cdot \tan(2\varepsilon)$ and d can correspond to the distance between the reflection point on the deformed cover and the sensor unit 5. As shown in FIG. 2c, the total shift s of the reflected light beam 6 of the non-pressurized state to a reflected light beam 6' of the pressurized state by a deformation of the cover 2 can be given by $s = s_1 + s_2$.

This can correspond to a linear mode of calculation, wherein the total shift s can be linear in relation to the pressure in the fluidic chamber 1 approximately. Of course more sophisticated calculation modes may be used. Also the mode of calculation can be based on a point-shaped light beam. In practice, in particular when using an LED as light emitter 3, the light beam can be a bundle of parallel light beams comprising a diameter $D_{lb}$. For using the calculation, the beam diameter $D_{lb}$ can be selected such that light at the edge of the bundle does not extend over the center point of the deformable cover 2. The maximum bundle diameter $D_{max}$ can fulfill the following requirement: $D_{lb} \leq 0.58 \sin(\alpha) D_{cov}$, wherein $D_{cov}$ can be the diameter of the deformable cover 2. The diameter $D_{cov}$ can be measured from a center point of the deformable cover in direction of the inflexion point area chosen for reflecting the incident light beam.

The dual-element sensor 5 can generate two separated singular raw signals $S_1$ and $S_2$, one signal $S_1$ of the photodiode 5a and a second signal $S_2$ of the photodiode 5b. In the case of a point-shaped light beam, for example, as emitted by a laser diode, the dual element sensor can generate a binary sensor signal S that is one of the raw signals can be on and the other one of the raw signal can be off. This can be because only one of the photodiodes 5a and 5b can be energized by the point-shaped light beam at a time. When using a LED as light emitter 3 comprising a bundle of parallel light beams with a diameter $D_{lb}$ a gradual shift from one photodiode 5a to the other photodiode 5b can occur.

Figure 3A:
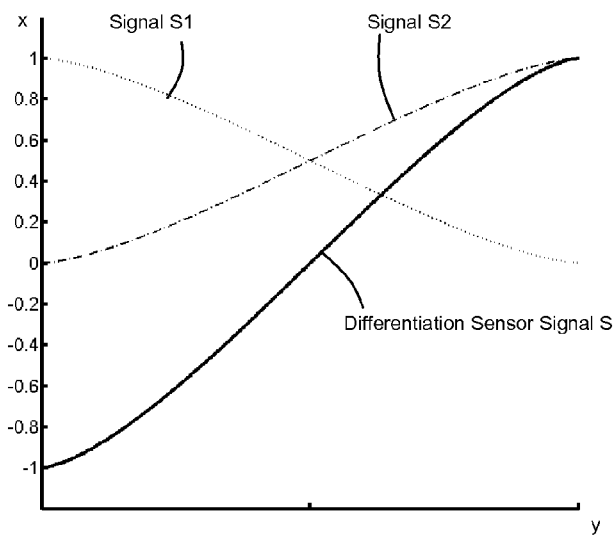
FIG. 3a illustrates a diagram of sensor signals of a sensor device using sensor unit comprising a dual-element sensor according to an embodiment of the present disclosure.

FIG. 3a illustrates the characteristics of the raw signals $S_1$ and $S_2$ and a differentiation signal S when a center of the beam bundle is shifted from one center point on photodiode 5a to the adjacent center point on photodiode 5b during deformation of the cover 2. The y-axis can indicate the value of the sensor signals and the x-axis can indicate the position of the center of the light bundle on the sensor 5. While the beam bundle is centered on the first photodiode 5a, raw signal $S_1$ can have the value 1 and raw signal $S_2$ can have the value 0. During the deformation of the cover 2, the beam bundle can wander to the center of the second photodiode 5b, where raw signal $S_1$ can have the value 0 and raw signal $S_2$ can have the value 1. By differentiation $S_2-S_1$ of the two raw signals, the sensor signal S can be extracted, which can be sufficiently linear in the area of transition between the two photodiodes. Such calculation model can allow a quantitative determination of the pressure values in the fluidic chamber.

In practice, the exact development of the sensor signal S and the behavior of the reflected light beam can depend on the relative positioning between the disposable unit and the reusable unit. The positioning usually can lie within a tolerance of about ±0.2 mm and may be different for each disposable unit. Therefore, after placing a new disposable unit on the reusable unit the sensor signal S can be taken as a reference value, wherein the fluidic pressure on the deformable cover can be about 0 bar relative to the atmosphere. The reference value can allow the integration of the absolute position of the cover before starting the operation of the medical fluid delivery system in the calculation model. Afterwards, the usual operation of the system can start, for example, by priming the fluidic path of the system with fluid.

Figure 3B:
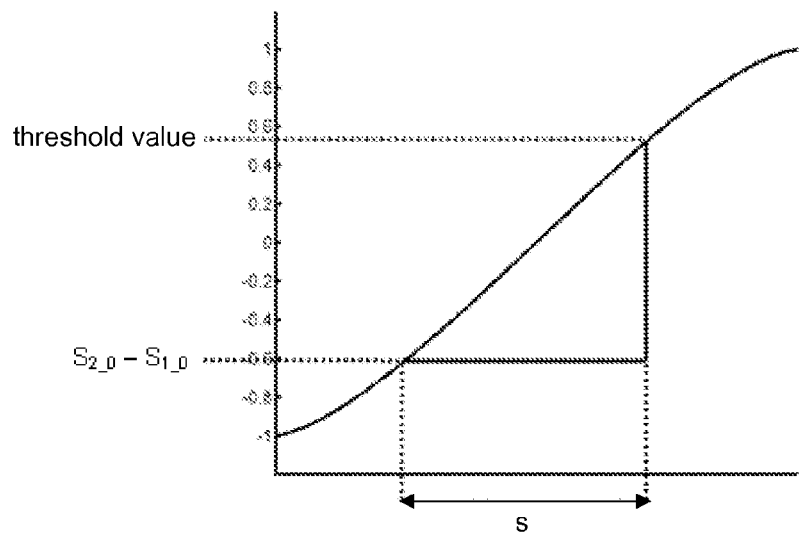
FIG. 3b illustrates a diagram of an algorithm to determine a threshold pressure value in accordance to a reference pressure value according to an embodiment of the present disclosure.

In case the sensor device is used as an occlusion sensor for detecting occlusion of the fluidic path, for example, for a medical fluid delivery system or an infusion pump device, a characteristic occlusion threshold value can be defined indicating an occlusion. In an algorithm, the threshold value may be defined as a fixed value. Alternatively, the threshold value of the differentiation sensor signal can be a function of the reference value. Thus, an influence of disturbing factors, like temperature effects or tolerance variations, can be minimized, which can mean the threshold value corresponding to occlusion can vary as little as possible. One possibility can be to calculate the threshold value of the differentiation sensor signal for each disposable unit at the beginning of the use of the disposable unit by involving the reference value and finally save the threshold value as fixed value. Again the characteristics according to FIG. 3a can be used to describe the sensor signal S. An expected shift s of the reflected light beam, which can correspond to an occlusion, can be known. Therefore based on the reference value, the expected shift s and the characteristics of the sensor signal S, the threshold value of the differentiation sensor signal for the occlusion can be determined as shown in FIG. 3b. The corresponding occlusion requirement can be:

$$S_2-S_1 \geq (S_{2\_0}-S_{1\_0})+m \cdot s$$

wherein $S_1$ can be the raw signal of the first photodiode, $S_2$ can be the raw signal of the second photodiode, $S_{1\_0}$ can be the reference value of the first photodiode at about 0 bar, $S_{2\_0}$ can be the reference value of the second photodiode at about 0 bar, m can be the inclination of the characteristics of the sensor signal S in a linear range, and s can be the expected shift of the reflected light beam on the sensor unit.

Another possibility to determine the threshold value of the differentiation sensor signal can be to save the reference value of the specific disposable unit and calculate the threshold value at the time of detection.

Non-linear effects in determining an occlusion threshold value can be minimized for example by involving results of experimental investigations. Experiments have shown that a required correction of a threshold value can be bigger, the higher the difference between a reference value and a nominal value corresponding to an ideal situation is. One possible algorithm for defining an occlusion pressure value based on experimental investigations can involve only the reference value $S_{1\_0}$ of the first photodiode and can be described by a hyperbolic relation as follows:

$$S_2-S_1 \geq (a/S_{1\_0})+c$$

wherein a can correspond to an empirical weighting and c can correspond to an offset value. The weighting factor a can minimize unwanted non-linear factors in the relevant range of the sensor signal characteristics. The offset value c can control the desired threshold value. The weighting factor a and the offset value c can have a specific design of the sensor device taking into account different basic conditions, such as, for example, thickness of the cover, diameter of the cover, reflectivity of the cover, and the like. Generally, the threshold value for an occlusion can be within the range of about 300 mbar and about 1500 mbar. Furthermore a temperature factor can be taken into consideration. A temperature sensor can be used to determine temperature changes, which can be located close to the interface between the disposable and reusable unit. Alternatively, a forward voltage of the LED may be used as temperature sensitive value.

In FIGS. 4 to 8, different embodiments of a sensor device are shown, wherein a light emitter 3 does not focus an incident light beam 4 directly on the deformable cover 2 but one or more optical elements can be, for example, part of a disposable unit of a medical fluid delivery system, which can deflect the light beam 4' of the light emitter and can direct it as the incident light beam 4 in a predetermined angle on the deformable cover. The incident light beam may reach the deformable cover in an angle between about 30° and about 60° or, in another embodiment, in an angle between about 40° and about 50°. Furthermore, an optical element can be in an optical path from the inflexion point area 12 towards one or both of first and/or second photodiodes. These optical elements can deflect the reflected light beam 6 of a non-pressurized state and the reflected light beam 6' of a pressurized state such that they can be directed to the sensor unit. The optical elements may be separate elements or realized in an optical unit including several optical elements. The material of the optical elements or unit can be mostly transparent, for example, an amorphous polymer may be used. Advantageously, the optical elements or unit can be made of the same material as the fluidic module 9. In general, the optical elements or unit can be adjusted relative to the deformable cover 2. Such optical elements or units may be used in combination with light emitters 3, which can be in a reusable unit of a medical fluid delivery system and can emit light beams perpendicular to the deformable cover 2. On the reflection side, the reflected light beams may be deflected by the optical elements or unit such that the reflected light beam can perpendicularly enter the reusable unit or the optical window 8 thereof.

Using optical elements can allow that the transition of the light beams between a disposable and a reusable unit of a medical fluid delivery system can be generally perpendicular, which can facilitate positioning of disposable and reusable unit relative to each other, in particular along an orientation perpendicular to the interface surfaces. Furthermore, the optoelectronic parts of the sensor device, like the light emitter and the sensor unit, can be in the reusable unit and can also be in small and narrow constructions of a reusable unit.

In general, it can be possible to select only a part of the light emitted by the light emitter 3, which can correspond to the direction focusing on the inflexion point area 12 of the cover 2. Thus, the lateral position of the disposable unit relative to the reusable unit along the surface of the deformable cover can allow more flexibility and tolerances can be larger. For example, a light-shaping element may be used to confine the emitted light beam.

Figure 4:
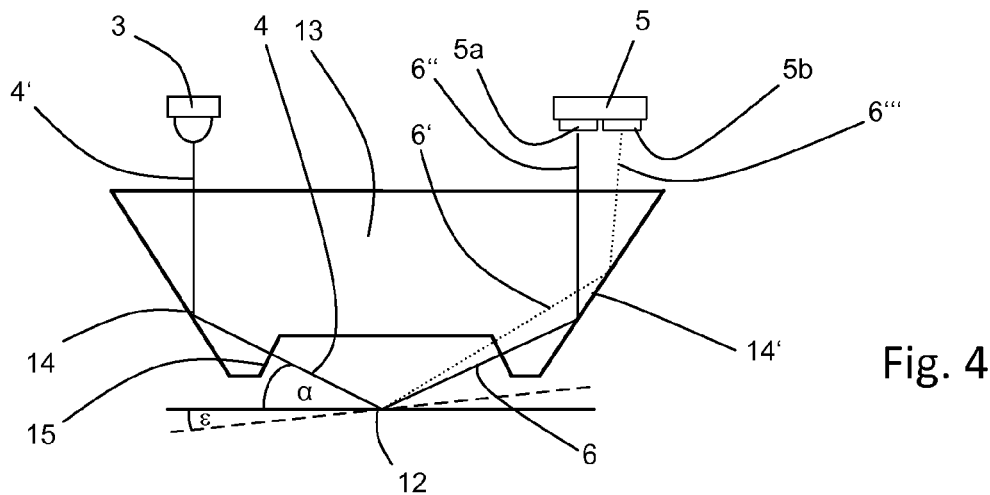
FIG. 4 illustrates schematically a first embodiment of a sensor device using optical elements to direct incident and reflected light beams according to an embodiment of the present disclosure.

In FIG. 4, a first embodiment of a sensor device is shown using an optical unit 13 to direct the incident and the reflected light beams to and from the inflection point area 12 of the deformable cover 2. The light path of the light beam according to a non-pressurized state is shown as a solid line. The light beam 4' emitted by the light emitter 3 can enter the optical unit 13 perpendicularly and can be reflected at an optical element 14 within the optical unit 13 comprising an angled reflection surface, such that an incident light beam 4 can exit the optical unit 13 at an angle α towards the deformable cover 2. A minor optical element can be used, for example. An exiting surface 15 can be orientated perpendicular to the incident light beam 4. Alternatively, the surface can be a refracting optical element and such can contribute to the alignment of the incident light beam. The incident light beam 4 can be reflected at the inflexion point area 12. The reflected light beams 6 and 6' can be directed back to the optical unit 13, can enter the optical unit 13 generally perpendicular and can be reflected at a second optical element 14' within the optical element 13. The reflected light beam 6" according to a non-pressurized state can be reflected on the optical element 14', can exit the optical element 13 and can perpendicularly meet the first photodiode 5a of the sensor unit 5. The light path according to a pressurized state is shown as pointed line. The deformation of the deformable cover 2 can deflect the reflected light beam 6'. Therefore, the reflected light beam 6' can be reflected at the optical element 14' offset from the reflected light beam 6 and can be guided towards the photodiode 5b as reflected light beam 6'".

Figure 5:
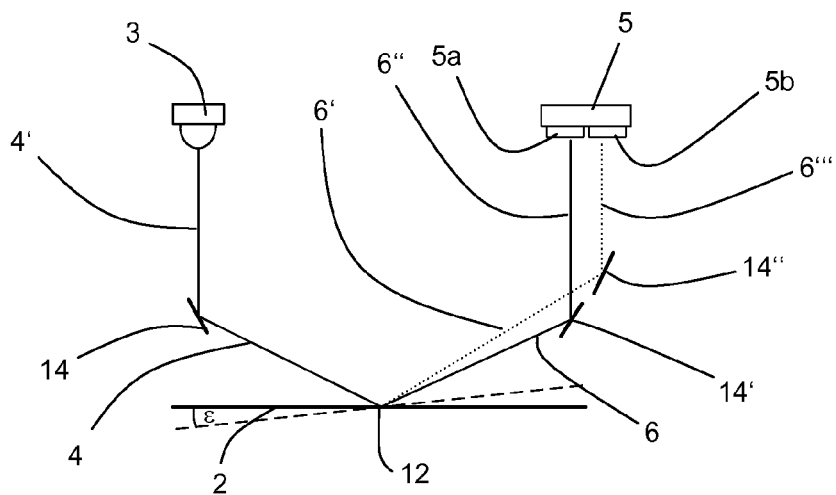
FIG. 5 illustrates schematically a second embodiment of a sensor device using optical elements according to an embodiment of the present disclosure.

In FIG. 5, a second embodiment of a sensor device is shown, which is similar to one of FIG. 4. But the optical elements for guiding the light beams can be separated from each other instead of being part of an optical unit 13. A first optical element 14 can be used to reflect the light beam 4' of the light emitter 3. A second optical element 14' can be used to reflect the reflected light beam 6 in direction to photodiode 5a. And a third optical element 14" can be used to reflect the shifted reflected light beam 6' in direction to photodiode 5b. The single optical elements 14, 14' and 14" can be oriented individually from each other.

Figure 6:
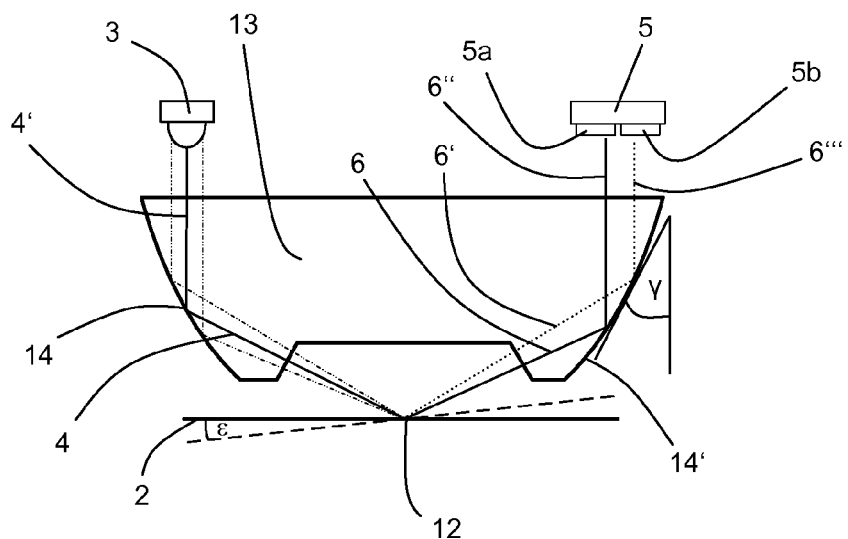
FIG. 6 illustrates schematically a third embodiment of a sensor device using optical elements according to an embodiment of the present disclosure.

In FIG. 6, a third embodiment of a sensor device is shown, which can comprise an optical unit 13 with optical elements 14 and 14' in form of a convex free-forming surface. A bundle of light beams 4' emitted by the light emitter 3 can be reflected at the optical element 14 and simultaneously the bundle of light beams 4' can be focused on the inflexion point area 12 on the deformable cover 2 by the convex form of the free forming surface. The reflected light beams 6 and 6' can be reflected at the convex free-forming surface of the optical element 14'. Due to the convex form the reflected light beam 6" (non-pressurized state) and also the reflected light beam 6'" (pressurized state) can run parallel to each other and perpendicular to the sensor unit 5. The angle γ at the reflection point of the optical element 14' to focus the reflected light beams 6" and 6'" on the sensor unit 5 can be for example defined as γ=45°−½ (α+δ).

Figure 7:
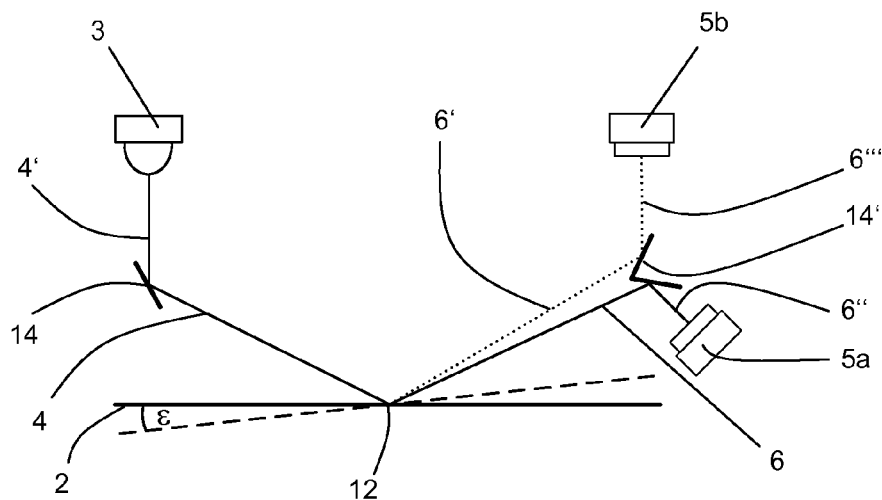
FIG. 7 illustrates schematically a fourth embodiment of a sensor device using optical elements for splitting reflected light beams according to an embodiment of the present disclosure.
Figure 8:
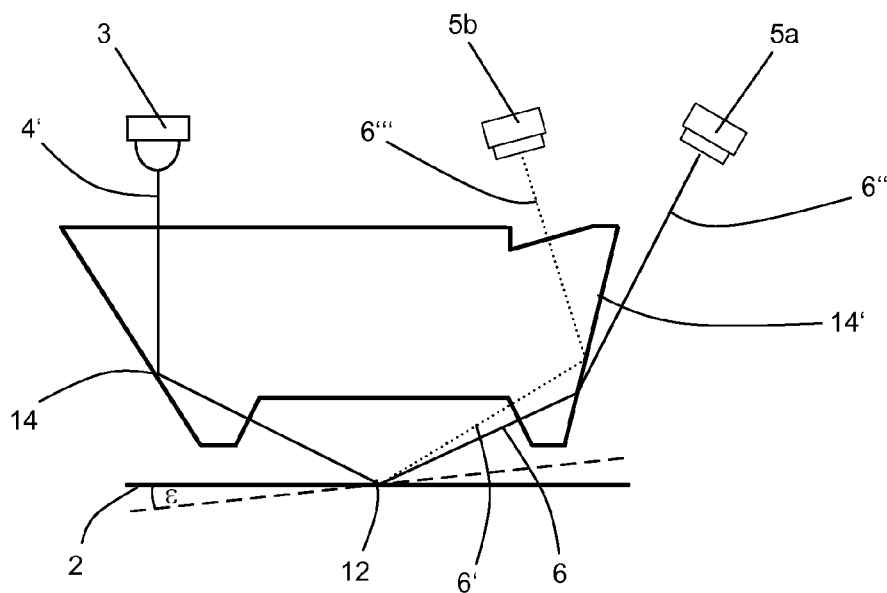
FIG. 8 illustrates schematically a fifth embodiment of a sensor device using optical elements for splitting reflected light beams according to an embodiment of the present disclosure.

The sensor devices as shown in FIGS. 7 and 8 can be advantageously used for the detection of an occlusion of a medical fluid delivery system. The reflected light beam reflected from the deformable cover 2 can be deflected at an optical element in largely different directions for a reflected light beam 6 reflected at a non-deformed cover 2 and for a reflected light beam 6' reflected at a deformed cover 2. That can mean the photo-elements 5a and 5b of the dual-element sensor 5 can be arranged individually and apart from each other.

In FIG. 7, the incident light beam can be directed to the deformable cover 2 as shown in FIG. 5. The reflected light beams 6 and 6' can be directed to an angled optical element 14' comprising two reflecting planes, which can be orientated in an angle towards each other. In a non-pressurized state, the reflected light beam 6 can be directed to a first plane of the optical element 14', which can reflect the reflected light beam 6" to the photodiode 5a. In a pressurized state, the reflected light beam 6' can be directed to a second plane of the optical element 14', which can reflect the reflected light beam 6'" to the photodiode 5b. The reflected light beams 6" and 6' can be nearly directed in opposite directions. The angle between first and second plane may be in a desired location of the photodiodes 5a and 5b or according to space requirements in the reusable unit.

In FIG. 8, the incident light beam can be directed to an optical unit 13, which can comprise an optical element 14' in the form of an optical surface, which can act as a refraction surface for reflected light beams reflected in a non-deformed state of the deformable cover 2 and can act as a reflection surface for reflected light beams reflected in a deformed state of the deformable cover 2. In particular, the optical surface may be designed such that the reflected light beam can be reflected at the optical element 14' as soon as the deformation of the deformable cover 2 can correspond to the occlusion threshold value indicating an occlusion condition of the fluidic module 9. Also the sensor unit 5 may comprise a third photodiode, which can be energized by a light beam reflected on the deformable cover 2 in a state in between the non-pressurized state and the pressurized state and can be refracted at the optical surface in direction of the third photodiode.

Figure 9:
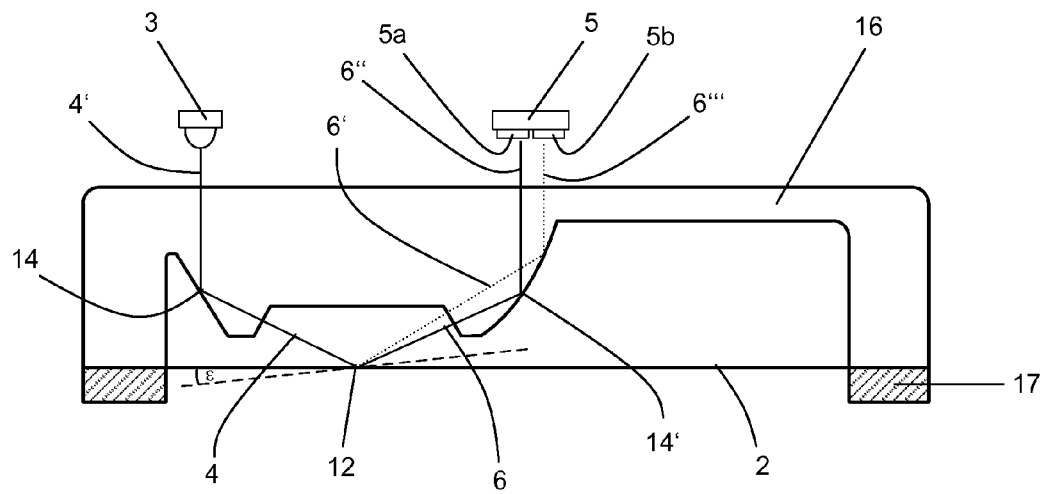
FIG. 9 illustrates a schematic cross-sectional view of a first embodiment of a covering of a disposable unit of a medical fluid delivery system comprising optical elements to direct incident and reflected light beams according to an embodiment of the present disclosure.
Figure 10:
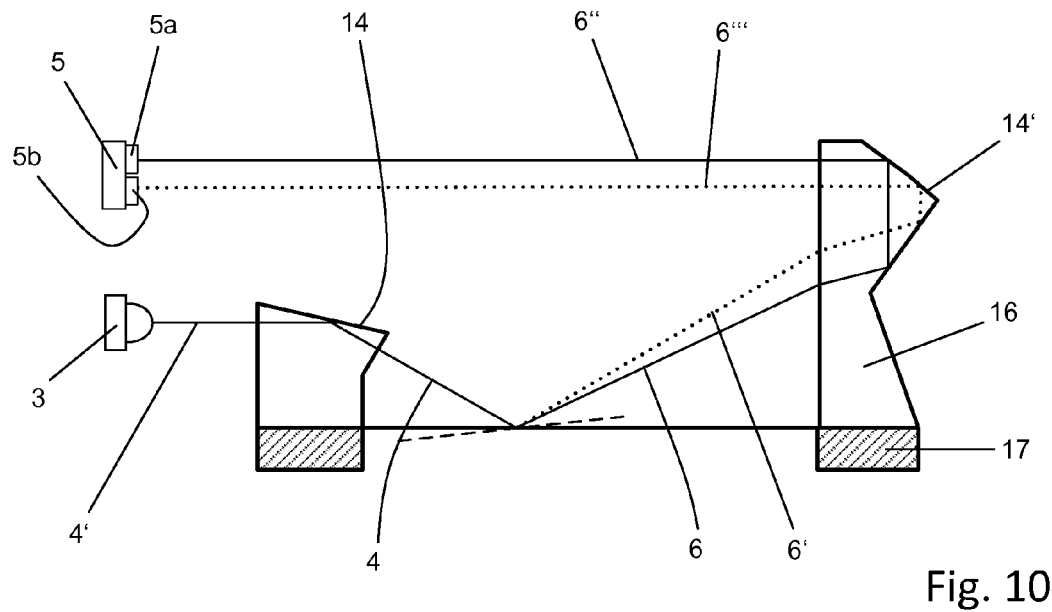
FIG. 10 illustrates a schematic cross-sectional view of a second embodiment of a covering of a disposable unit of a medical fluid delivery system comprising optical elements according to an embodiment of the present disclosure.

In FIGS. 9 and 10, sensor devices for use in a medical fluid delivery system are shown, wherein optical elements 14 and 14' can be part of a cap or covering 16 of the fluidic module 9, which can be attached to a surrounding edge 17 of the fluidic module. As shown in FIG. 9, the covering 16 can extend between the optoelectronic parts arranged in the reusable unit of the medical fluid delivery system and the deformable cover 2 and can stretch between the edges 17. In the direction towards the deformable cover 2, the covering 16 can be designed according to an optical unit as shown in FIG. 4 or 6 respectively and can provide optical elements 14 and 14' to direct the incident light beams 4 and 4' and the reflected light beams 6, 6', 6" and 6'".

In FIG. 10, an embodiment of the sensor device is shown, wherein the light emitter 3 can emit a light beam 4' and the sensor unit 5 can receive reflected light beams 6" and 6'" parallel to cover 2. That can mean the optoelectronic parts in the reusable unit can be located on a side of the disposable unit instead of opposite to it. The fluidic module can comprise optic elements 14 and 14', wherein a first prism 14 can direct the light beam 4' of the light emitter 3 as an incident light beam 4 on the inflexion point area 12 of the deformable cover 2 and a second prism 14' in the form of a double prism can direct the reflected light beams 6" and 6''' to the sensor unit 5. The prism 14' can be designed such that the light beam 6 reflected in a non-pressurized state of the deformable cover 2 can be directed to the photodiode 5a and the light beam 6' reflected in a pressurized state of the deformable cover 2 can be directed to the photodiode 5b.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

The present disclosure has been described in respect of several embodiments of a sensor device. The present invention is not to be limited in scope by the specific embodiments described herein. Of course the features according to specific described embodiments may be combined to further embodiments by a person skilled in the art although not explained in detail herein. Indeed, various modifications of the present invention, in addition to those described herein, will be apparent to those skilled in the art from the foregoing description and accompanying drawings. Thus, such modifications are intended to fall within the scope of the appended claims. Additionally, various references are cited throughout the specification, the disclosures of which are each incorporated herein by reference in their entirety.

We claim:

1. A sensor device for use in a medical fluid delivery system, the sensor device comprising:
    a fluidic chamber with a deformable cover closing at least an area of the fluidic chamber, wherein, in a pressurized state of the fluidic chamber, the deformable cover is deformed such that it forms an inflexion point area within the deformed cover; and
    an optical detection system comprising at least one light emitter for emitting one or more incident light beams and a sensor unit for monitoring one or more reflected light beams, wherein the one or more incident light beams emitted by the light emitter are directed on the cover such that the one or more incident light beams are reflected in the inflexion point area.

2. The sensor device according to claim 1, wherein the one or more incident light beams are directed on the cover at an angle α.

3. The sensor device according to claim 1, wherein the light emitter of the sensor device is located on a side of the cover which is curved in a convex manner in an increased pressure state of the fluidic chamber.

4. The sensor device according to claim 3, wherein one side of the cover is in fluid contact and the light emitter is located on the other side of the cover.

5. The sensor device according to claim 1, wherein the incident light beam is a parallel light beam.

6. The sensor device according to claim 1, wherein the light emitter is a laser diode comprising an optical element for parallelizing emitted light beams.

7. The sensor device according to claim 1, wherein the light emitter is a light emitting diode comprising an optical element for parallelizing emitted light beams.

8. The sensor device according to claim 1, wherein the sensor unit is a dual-element sensor with two photo-elements.

9. The sensor device according to claim 8, wherein an optical element is provided in an optical path from the inflexion point area towards one or both of first and/or second photo-elements.

10. The sensor device according to claim 1, wherein a diameter of an overall incident light beam is selected such that an edge of the beam does not extend beyond a center point of the cover.

11. The sensor device according to claim 1, wherein the cover covers an at least partially rounded opening of the fluidic chamber.

12. The sensor device according to claim 1, wherein the one or more incident light beams are reflected at an inflection point area located closest to the light emitter.

13. An infusion pump device for use in a medical fluid delivery system, the infusion pump device comprising a sensor device according to claim 1.

14. A medical fluid delivery system, the medical fluid delivery system comprising a sensor device according to claim 1.

15. The medical fluid delivery system according to claim 14, wherein the optical detection system is part of a reusable unit of the delivery device and the fluidic chamber is part of a disposable unit of the delivery device and wherein the disposable unit comprises an optical element for directing the incident light beam in an angle α on the inflexion point area of the cover.

16. The medical fluid delivery system according to claim 15, wherein the disposable unit comprises an optical element for directing the reflected light beam from the inflexion point area to the sensor unit.

17. A disposable unit for use with a medical fluid delivery system, wherein an optical element for directing an incident light beam of a sensor device in an angle α on an inflexion point area of a deformable cover of a fluidic chamber.

18. A method for monitoring a pressure change in a fluidic chamber of a medical fluid delivery system using a sensor device according to claim 1, comprising:
    directing one or more incident light beams on the inflexion point area of the deformable cover;
    detecting one or more reflected light beams reflected from the deformable cover in a non-pressurized state and a pressurized state; and
    comparing detection data of the non-pressurized state and the pressurized state to extract the pressure change value.

* * * * *